(12) United States Patent
Shorr et al.

(10) Patent No.: US 8,691,873 B2
(45) Date of Patent: *Apr. 8, 2014

(54) PHARMACEUTICAL FORMULATIONS CONTAINING LIPOIC ACID DERIVATIVES

(75) Inventors: Robert G. L. Shorr, Edison, NJ (US); Robert J. Rodriguez, West Windsor, NJ (US); Rajinder Bhasin, Coram, NY (US)

(73) Assignee: Cornerstone Pharmaceuticals, Inc., Cranbury, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/253,503

(22) Filed: Oct. 5, 2011

(65) Prior Publication Data

US 2012/0178812 A1 Jul. 12, 2012

Related U.S. Application Data

(63) Continuation of application No. 12/105,100, filed on Apr. 17, 2008, now abandoned.

(60) Provisional application No. 60/912,605, filed on Apr. 18, 2007.

(51) Int. Cl.
*A61K 31/205* (2006.01)

(52) U.S. Cl.
USPC .......................................... 514/555; 514/554

(58) Field of Classification Search
None
See application file for complete search history.

(56) References Cited

U.S. PATENT DOCUMENTS

| | | | |
|---|---|---|---|
| 2,805,251 A | 9/1957 | Marshall et al. | |
| 2,809,978 A | 10/1957 | Holly et al. | |
| 2,852,531 A | 9/1958 | Hoffman et al. | |
| 2,875,238 A | 2/1959 | Holly et al. | |
| 2,875,239 A | 2/1959 | Holly et al. | |
| 2,975,198 A | 3/1961 | Reed | |
| 2,980,716 A | 4/1961 | Reed | |
| 2,985,685 A | 5/1961 | Thomas et al. | |
| 3,002,011 A * | 9/1961 | Holly et al. | 554/102 |
| 3,345,368 A | 10/1967 | Lewis et al. | |
| 3,453,312 A | 7/1969 | Sprague | |
| 3,881,017 A | 4/1975 | Vlattas | |
| 3,970,670 A | 7/1976 | Vlattas | |
| 4,041,047 A | 8/1977 | Vlattas | |
| 4,077,979 A | 3/1978 | Vlattas | |
| 4,077,980 A | 3/1978 | Vlattas | |
| 4,705,867 A | 11/1987 | Giray et al. | |

(Continued)

FOREIGN PATENT DOCUMENTS

| | | |
|---|---|---|
| GB | 758897 | 10/1956 |
| JP | 2007077066 A | 3/2007 |
| JP | 4728481 B2 | 7/2011 |
| WO | WO-00/24734 | 5/2000 |

OTHER PUBLICATIONS

Patani et al.; "Bioisosterism: A Rational Approach in Drug Design"; 1996; Chem. Rev.; 96:3147-3176.*

(Continued)

*Primary Examiner* — Timothy Thomas
(74) *Attorney, Agent, or Firm* — Goodwin Procter LLP

(57) ABSTRACT

The invention provides a method of treating leukemia using a pharmaceutical composition containing bis-benzyl lipoate, triethanolamine, and a pharmaceutically acceptable diluent, where the bis-benzyl lipoate and triethanolamine form an ion pair.

4 Claims, 2 Drawing Sheets

Tumor Volume in H-460 Tumor-Bearing Mice Treated with IP CPI-613

- ● Injected 1x weekly
- ■ Injected 5x weekly
- ▼ Injected 3x weekly
- ▲ Vehicle, injected 5x weekly (shown in all 3 graphs)

(56) References Cited

U.S. PATENT DOCUMENTS

| | | | |
|---|---|---|---|
| 4,800,044 | A | 1/1989 | Giray et al. |
| 4,966,732 | A | 10/1990 | Giray et al. |
| 5,344,941 | A | 9/1994 | Samour et al. |
| 5,463,093 | A | 10/1995 | Garnett |
| 5,508,275 | A | 4/1996 | Weithmann et al. |
| 5,569,670 | A | 10/1996 | Weischer et al. |
| 5,679,697 | A | 10/1997 | Garnett |
| 5,750,141 | A * | 5/1998 | Roberts et al. ............... 424/449 |
| 6,117,902 | A | 9/2000 | Quash et al. |
| 6,331,559 | B1 | 12/2001 | Bingham et al. |
| 6,951,887 | B2 * | 10/2005 | Bingham et al. ............. 514/557 |
| 8,263,653 | B2 | 9/2012 | Shorr et al. |
| 2005/0048008 | A1 | 3/2005 | Gupta |
| 2008/0262034 | A1 | 10/2008 | Bingham et al. |
| 2008/0262077 | A1 | 10/2008 | Shorr et al. |
| 2009/0036356 | A1 | 2/2009 | Patell et al. |

OTHER PUBLICATIONS

Berge et al.; "Pharmaceutical Salts"; 1997; Journal of Pharmaceutical Sciences; 66(1): 1-19.*
Kintzel et al.; "Practical guidelines for preparing and administering amphotericin B"; 1992; Am. J. Hosp. Pharm.; 49(5): 1156-64; Pub Med abstract.*
Adams (1955) "Thioctic-$S^{35}_2$ Acid: Synthesis and Radiation Decomposition" *J. Am. Chem. Soc.* 77:5357-5359.
Crévisy et al. (1998) "A New Iron-Mediated Strategy for the Synthesis of α-Lipoic Acid and Analogues" *Eur. J. Org. Chem.* pp. 1949-1954.
Daigo et al. (1962) "Synthesis of Some N-Lipoyl Amino Acids and Peptides" *J. Am. Chem. Soc.* 84(4):662-665.
Heather A. E. Benson (2005) "Transdermal Drug Delivery: Penetration Enhancement Techniques" *Current Drug Deliver*, vol. 2, No. 1, pp. 23-33.
International Preliminary Report on Patentability for International Application No. PCT/US2008/060650 (6 pages).
International Search Report for International Application No. PCT/US2008/060650 mailed Jul. 18, 2008 (1 page).
Kieler et al. (1967) "The Effect of Structural Analogues of α-lipoic Acid on the Growth and Metabolism of L-Fibroblasts and Ehrlich Cells" *Archivum lmmunologiae et Therapiae Experimentalis*, vol. 15, pp. 106-108.
Nakano et al. (1955) "Studies on α-Lipoic Acid and its Related Compounds. I. Synthesis of DL-α-Lipoic Acid" *Yakugaku Zass*, 75(10):1296-1298. (with English abstract).
Nakano (1956) "Studies on a-Lipoic Acid and its Related Compounds. IV. On Acetylation of Ethyl DL-Dihydro-α-lipoate" *Yakugaku Zasshi*, 76(10):1207-1209. (with English abstract).
Pan et al. (1998) "D,L-S-Methyllipoic Acid Methyl Ester, a Kinetically Viable Model for S-protonated Lipic Acid as the Oxidizing Agent in Reductive Acyl Transfers Catalyzed by the 2-Oxoacid Dehydrogenase Multienzyme Complexes" *Biochemistry* 37(5):1357-1364.
Rastetter et al. (1981) "α-Keto Acid Dehydrogenases: A Chemical Model" *J. Org. Chem.* 46(9): 1882-1887.
Reed et al. (1955) "Synthesis of DL-α-Lipoic Acid" *J. Amer. Chem. Soc.* 77:416-419.
Schoberl et al. (1958) *Justus Liebigs Ann. Chem.* 614:66-83.
Shih et al. (1974) "Properties of Lipoic Acid Analogs" *J. Heterocycl. Chem.* 11:119-123.
Soper et al. (1954) "Syntheses of DL-α-Lipoic Acid" *J. Am. Chem. Soc.* 76:4109-12.
Supplementary European Search Report and Search Opinion mailed May 19, 2010 in European Patent Application No. 08780538 (7 pages).
Surya Kanta De, "Yttrium Trifflate as an Efficient and Useful Catalyst for Chemoselective Protection of Carbonyl Compounds" *Tetrahedron Letters*, vol. 45, pp. 2339-2341 (2004).
Thomas et al. (1955) "Synthesis and Properties of High Specific Activity DL-α-Lipoic Acid-$S_2^{35}$" *J. Am. Chem. Soc.* 77(20):5446-5448.
Thomas et al. (1956) "Synthesis of DL-1,2-Dithiolane-3-Caproic Acid and DL-1,2-Dithiolane-3-Butyric Acid, Homologs of α-Lipoic Acid" *J. Am. Chem. Soc.* 78(23):6151-6153.
Watabe et al. (2007) "ATP Depletion Does Not Account for Apoptosis Induced by Inhibition of Mitochondrial Electron Transport Chain in Human Dopaminergic Cells" *Neuropharmacology* 52(2):536-541.
English Translation of Nakano et al. in *Yakugaku Zasshi* (1956), 76, 943-7.
T. Higuchi and K. Kato, *J. Pharm. Sci.* (1966) vol. 55, pp. 1080-1084.
T. Higuchi et al., *Anal. Chem.* (1967) vol. 39, pp. 974-979.
A.F. Michaelis and T. Higuchi, in *J. Pharm. Sci.* (1969) vol. 58, pp. 201-204.
Kintzel et al. "Practical guidelines for preparing and administering amphotericin B", 1992, *Am. J. Hosp. Pharm.*, 49(5): 1156-64, Pub Med abstract, PMID: 1595747.
Bastin et al. (2000) "Salt Selection and Optimisation Procedures for Pharmaceutical New Chemical Entities" *Organic Process Research & Development*, vol. 4, pp. 427-435.
Automated CellTiter-Glo® Luminescent Cell Viability Assay Protocol, *Promega*, Part # EP014, (2009).
National Toxicology Program (NTP) (2003). Toxicology and Carcinogenesis Studies of Triethanolamine (CAS No. 102-71-6) in F344/N Rats and B6C3F1 Mice (Dermal Studies), NTP TR 518, NIH Publication No. 03-4452.
Search Report from European Patent Application No. 08780538.8 mailed Feb. 24, 2012 (5 pages).
Serajuddin (2007) "Salt formation to improve drug solubility" *ScienceDirect, Advanced Drug Delivery Reviews*, vol. 59, pp. 603-616.
Zong et al. (2006) "Necrotic death as a cell fate" *Genes & Development*, vol. 20, pp. 1-15.
Stott et al. (2004) "Evaluation of the Potential of Triethanolamine to Alter Hepatic Choline Levels in Female B6C3F1 Mice" *Toxicological Sciences*, vol. 79, pp. 242-247.
Johar D et al. (2004) "Inflammatory response, reactive oxygen species, programmed (necrotic-like and apoptotic) cell death and cancer" *Roczniki Akademii Medycznej w Bialymstoku*, vol. 49, *Annales Academiae Medicae Bialostocensis*, pp. 31-39.
International Search Report and Written Opinion for International Application No. PCT/US2010/053728 mailed Mar. 24, 2011 (9 pages).
Berge et al. (1997) "Pharmaceutical Salts," *Journal of Pharmaceutical Science*, 66(1), pp. 1-19.

* cited by examiner

PHARMACEUTICAL FORMULATIONS CONTAINING LIPOIC ACID DERIVATIVES

This application is a continuation of U.S. application Ser. No. 12/105,100, filed Apr. 17, 2008, which claims the benefit of U.S. Provisional Patent Application No. 60/912,605, filed Apr. 18, 2007, the entire disclosures of each of which are hereby incorporated by reference.

BACKGROUND OF THE INVENTION

1. Field of the Invention

The present invention is directed to pharmaceutical formulations containing lipoic acid derivatives or salts thereof which selectively kill tumor cells by altering cancer cell metabolism and signal transduction pathways linked to the Warburg Effect, as well as to methods of treating a subject with such pharmaceutical formulations.

2. Related Background Art

All mammalian cells require energy to live and grow. Cells obtain this energy by metabolizing food molecules by oxidative metabolism. The vast majority of normal cells utilize a single metabolic pathway to metabolize their food. The first step in this metabolic pathway is the partial degradation of glucose molecules to pyruvate in a process known as glycolysis which yields two ATP units. Glycolysis can occur even under hypoxic conditions. Pyruvate is further degraded in the mitochondrion by a process known as the tricarboxylic acid (TCA) cycle to produce thirty-six ATP units per glucose molecule, water and carbon dioxide. The TCA cycle requires oxygen. During periods of reduced oxygen levels, normal cells adapt by a variety of mechanisms and return to normal metabolism as oxygen levels are restored. A critical link between glycolysis and the TCA cycle is an enzyme known as pyruvate dehydrogenase ("PDH"). PDH is part of a larger multi-subunit complex (hereinafter "PDC"). PDH, in conjunction with other enzymes of the PDC complex, produces acetyl CoA which effectively funnels glycolysis-produced pyruvate to the TCA cycle.

Most cancers display profound perturbation of energy metabolism. One of the fundamental changes is the adoption of the Warburg Effect, where glycolysis becomes the main source of ATP. An ATP deficit follows reduced TCA ATP generation. In other words, cancer cells behave as if they are hypoxic even when they are not. This change in energy metabolism represents one of the most robust and well-documented correlates of malignant transformation and has been linked to other changes resulting in tumor growth and metastasis. Because of the reduced levels of ATP available as a result of glycolysis largely being de-linked from the TCA cycle, cancer cells increase their uptake of glucose and its conversion to pyruvate in an attempt to make up the energy deficit. Excess pyruvate and other metabolic by-products of the Warburg biochemistry must be managed. A number of these metabolites are known to be cytotoxic, e.g., acetaldehyde. PDC in cancer along with other related enzymes plays a major role in managing and/or detoxifying the excess pyruvate and metabolites. For example, the joining of two acetyl molecules to form the neutral compound acetoin. This generation of acetoin is catalyzed by a tumor-specific form of PDC. It has been suggested that lipoic acid acts as a cofactor with PDC and related lipoamide using enzymes in detoxifying these otherwise toxic metabolites. Whether lipoic acid is made by healthy and cancer cells or whether it is an essential nutrient is debated in the literature, and both may be the case. The genes required to produce lipoic acid have been identified in mammalian cells. Whether mitochondrial pumps or uptake mechanisms are present in healthy or cancer cells or whether they differ in diverse tissues is not known. Although the TCA cycle still functions in cancer cells, the tumor cell TCA cycle is a variant cycle which depends on glutamine as the primary energy source. Inhibition or inactivation of tumor-specific PDC and related enzymes that detoxify metabolites may promote apoptosis or necrosis and cell death.

Despite extensive work characterizing the highly conserved changes among diverse tumor types and their metabolism, the changes remain to be successfully exploited as a target for cancer chemotherapy. As cancer remains the number two killer of Americans, there is an urgent need for new approaches to disease management. It has been suggested that lipoic acid due to its redox potential properties may be useful in the treatment of diverse diseases involving mitochondrial function such as diabetes, Alzheimers disease and cancer. These reports teach that the availability of the redox shift from SH to S—S be maintained to have the desired effect.

U.S. Pat. Nos. 6,331,559 and 6,951,887 disclose a novel class of therapeutic agents which selectively targets and kills tumor cells and certain other types of diseased cells. These patents further disclose pharmaceutical compositions comprising an effective amount of a lipoic acid derivative according to its invention along with a pharmaceutically acceptable carrier. However, these patents provide no specific guidance with regard to the selection of suitable pharmaceutically acceptable carriers. As the present inventors have now discovered, the pharmaceutical formulation of the lipoic acid derivatives has proved pivotal in achieving efficacy for these agents.

SUMMARY OF THE INVENTION

In a first aspect, the present invention is directed to a pharmaceutical formulation comprising (a) at least one lipoic acid derivative or salt thereof and (b) at least one ion pairing agent and optionally (c) a pharmaceutically acceptable diluent. In a preferred embodiment of the invention, the lipoic acid derivative has the formula (I):

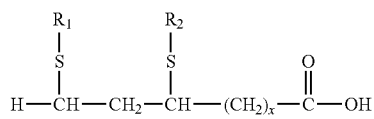

wherein $R_1$ and $R_2$ are independently selected from the group consisting of acyl defined as $R_3C(O)-$, alkyl defined as $C_nH_{2n+1}$, alkenyl defined as $C_mH_{2m-1}$, alkynyl defined as $C_mH_{2m-3}$, aryl, heteroaryl, alkyl sulfide defined as $CH_3(CH_2)_n-S-$, imidoyl defined as $R_3C(=NH)-$, hemiacetal defined as $R_4CH(OH)-S-$, and hydrogen provided that at least one of $R_1$ and $R_2$ is not hydrogen; wherein $R_1$ and $R_2$ as defined above can be unsubstituted or substituted; wherein $R_3$ is hydrogen, alkyl, alkenyl, alkynyl, cycloalkyl, aryl, alkylaryl, heteroaryl, or heterocyclyl, any of which can be substituted or unsubstituted; wherein $R_4$ is $CCl_3$ or $COOH$; and wherein x is 0-16, n is 0-10 and m is 2-10. In a preferred embodiment, $R_1$ and $R_2$ are both a benzyl group, i.e., both $R_1$ and $R_2$ are independently $-CH_2C_6H_5$. In another preferred embodiment, the lipoic acid derivative has the formula (II):

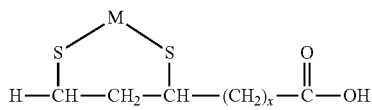

wherein M is a metal chelate, —[C(R₁)(R₂)]₂— or other metal complex; wherein R₁ and R₂ are independently selected from the group consisting of acyl defined as $R_3C(O)$—, alkyl defined as $C_nH_{2n+1}$, alkenyl defined as $C_mH_{2m-1}$, alkynyl defined as $C_mH_{2m-3}$, aryl, alkyl sulfide defined as $CH_3(CH_2)_n$—S—, imidoyl defined as $R_3C(=NH)$—, hemiacetal defined as $R_4CH(OH)$—S— and hydrogen; wherein R₁ and R₂ as defined above can be unsubstituted or substituted; wherein R₃ is hydrogen, alkyl, alkenyl, alkynyl, cycloalkyl, aryl, alkylaryl, heteroaryl, or heterocyclyl, any of which can be substituted or unsubstituted; wherein R₄ is $CCl_3$ or COOH; and wherein x is 0-16, z is 0-5, n is 0-10 and m is 2-10.

Further preferred embodiments of this invention include those in which the lipoic acid derivative is present in a therapeutically effective amount. Still further preferred embodiments of this invention include those in which the ion pairing agent is selected from the group consisting of triethanolamine, polyethyleneimine, monoethanolamine, diethanolamine, mefanamic acid, tromethamine and combinations thereof, those in which the ion pairing agent is a polymer-conjugated ion pairing agent, and those in which the ion pairing agent and the at least one lipoic acid derivative is present in a ratio ranging from about 1000:1 to about 1:1000. Further preferred embodiments of the present invention also include those in which the diluent is selected from the group consisting of saline, a sugar solution, an alcohol, dimethylformamide, dimethylsulfoxide, dimethylacetamide and combinations thereof.

In a second aspect, the present invention is directed to a method of treating a disease characterized by disease cells that are sensitive to lipoic acid derivatives comprising administering to a patient in need thereof a pharmaceutical formulation comprising at least one lipoic acid derivative or salt thereof, at least one ion pairing agent, and optionally a pharmaceutically acceptable diluent. In a third aspect, the present invention is directed to a method of preventing a disease characterized by disease cells that are sensitive to lipoic acid derivatives comprising administering to a patient in need thereof a pharmaceutical formulation comprising at least one lipoic acid derivative, at least one ion pairing agent, and optionally a pharmaceutically acceptable diluent. In preferred embodiments of these methods, the disease is a cancer such as a carcinoma, sarcoma, myeloma, lymphoma, leukemia, or a mixed cancer type.

In yet another aspect, the invention is directed to an ion pair consisting of (a) at least one lipoic acid derivative and (b) at least one ion pairing agent, most preferably bis-benzyl lipoate and triethanolamine, respectively.

DETAILED DESCRIPTION

Figures 1A, 1B:
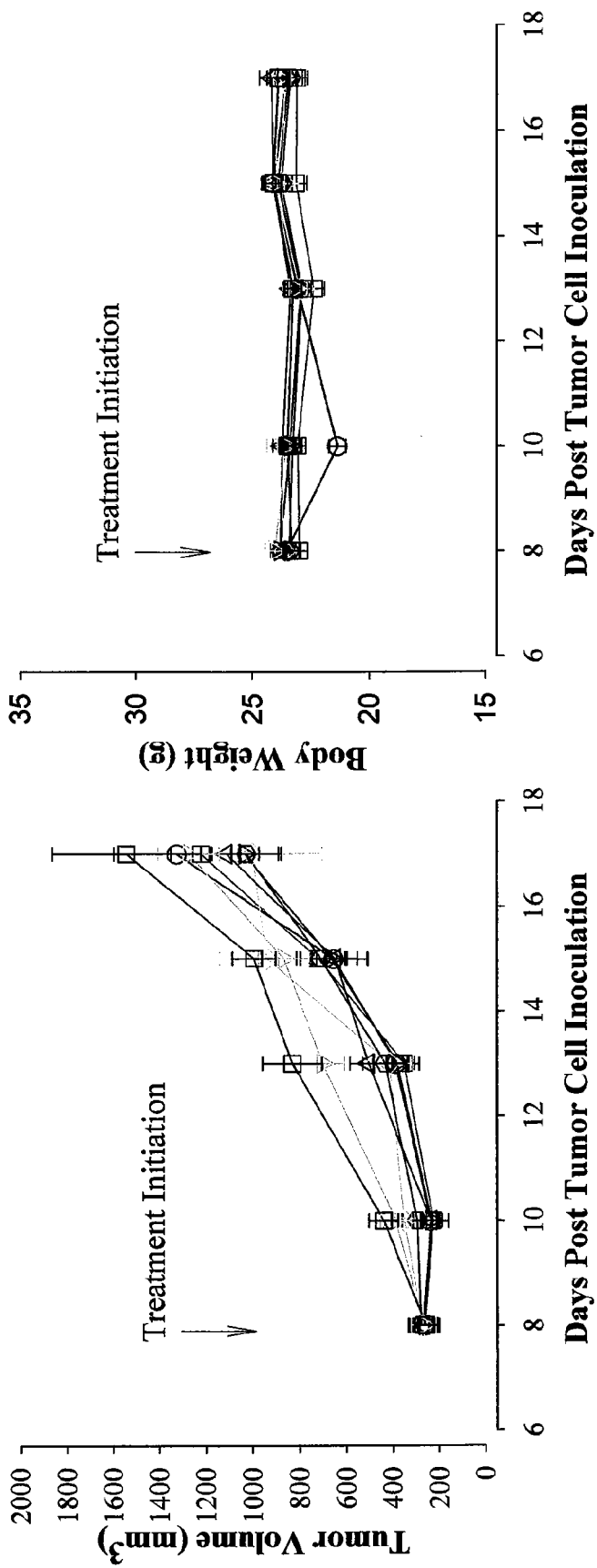
FIGS. 1A and 1B show the tumor volume and body weight, respectively, in H-460 tumor-bearing mice treated with bis-benzyl lipoate in a Tween 80/ethanol pharmaceutical formulation.

The present invention is directed to pharmaceutical formulations containing lipoic acid derivatives which are effective to target and kill tumor cells. While the pharmaceutical formulation of many therapeutic agents is quite conventional, the present inventors have found that the pharmaceutical formulation of lipoic acid derivatives is not. In fact, the particular pharmaceutical formulation in which a lipoic acid derivative is placed may well be the determining factor between inactivity and activity for its intended purpose. Accordingly, in a first embodiment, the present invention is directed to a pharmaceutical formulation comprising (a) at least one lipoic acid derivative and (b) at least one ion pairing agent and optionally (c) a pharmaceutically acceptable diluent.

Lipoic acid derivatives suitable for use in the present invention include those described in full detail in each of U.S. Pat. Nos. 6,331,559 and 6,951,887 and those described in co-pending U.S. Provisional Application No. 60/912,598, filed Apr. 18, 2007 and corresponding co-pending U.S. patent application Ser. No. 12/105,096, filed Apr. 17, 2008, the disclosure of each of which is incorporated by reference herein. Lipoic acid derivatives suitable for use in the present invention can be made according to known procedures such as those set forth in the aforementioned patents. In a preferred embodiment of this invention, the lipoic acid derivative has the formula (I):

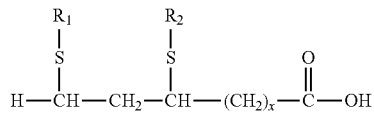

or a salt thereof;

wherein R₁ and R₂ are independently selected from the group consisting of acyl defined as $R_3C(O)$, alkyl defined as $C_nH_{2n+1}$, alkenyl defined as $C_mH_{2m-1}$, alkynyl defined as $C_mH_{2m-3}$, aryl, heteroaryl, alkyl sulfide defined as $CH_3(CH_2)_n$—S—, imidoyl defined as $R_3C(=NH)$—, hemiacetal defined as $R_4CH(OH)$—S—, and hydrogen provided that at least one of R₁ and R₂ is not hydrogen;

wherein R₁ and R₂ as defined above can be unsubstituted or substituted;

wherein R₃ is hydrogen, alkyl, alkenyl, alkynyl, cycloalkyl, aryl, alkylaryl, heteroaryl, or heterocyclyl, any of which can be substituted or unsubstituted;

wherein R₄ is $CCl_3$ or COOH; and wherein x is 0-16, n is 0-10 and m is 2-10.

As used herein, acyl refers to an $R_3C(O)$— group, where R₃ can be, without limitation, hydrogen, alkyl, alkenyl, alkynyl, cycloalkyl, aryl, alkylaryl, heteroaryl, or heterocyclyl, any of which can be substituted or unsubstituted. In other words, one of the listed R₃ groups is linked to the carbon backbone of formula (I) through a thio-ester linkage. Examples of acyl groups include, without limitation, acetyl, benzoyl and benzoyl derivatives, 4-fluorobenzoyl and 1-methylpyrrole-2-carboxyl. Specific examples of lipoic acid derivatives containing an acyl group include, without limitation, bis-acetyl lipoate and bis-benzoyl lipoate.

As used herein, alkyl refers to a $C_nH_{2n+1}$ group, wherein n is 1-10, more preferably 1-6 and most preferably 1-4, i.e., an alkyl group linked to the carbon backbone of formula (I) through a thio-ether linkage. Alkyl groups can be either aliphatic (straight or branched chain) or alicyclic; alicyclic groups may have additions or substitutions on any of the carbons to form heterocyclics. At least one heteroatom such as N, O or S may be present in a given alkyl group, i.e., in the carbon chain. Alkyl groups may be substituted or unsubstituted on any of their carbons. A preferred alkyl group is an alkyl group substituted with an aryl or heteroaryl group, i.e., wherein $R_1$ or $R_2$ is an alkylaryl or alkylheteroaryl group; the aryl or heteroaryl group may be substituted or unsubstituted. Examples of alkyl groups include, without limitation, methyl, ethyl, butyl, decanyl, cyclopropyl, 4-pyridine methyl, 2-anthraquinone methyl, N-phenylacetamide, phenylethyl, 2-ethanoic acid, 2-acetamido, 4-(2-acetamido-pyridinyl)methyl, N-[(2-fluorophenyl)methyl]acetamide, N-[(6-methoxy-3-pyridyl)methyl]acetamide, 5-(acetylamino)pyridine-2-carboxamide, 5-(6,8-diaza-7-oxo-3-thiabicyclo[3.3.0]oct-2-yl)-N-(2-carbonylaminoethyl)pentanamide and 5-(6,8-diaza-7-oxo-3-thiabicyclo[3.3.0]oct-2-yl)pentacarboxyl. Specific examples of lipoic acid derivatives containing an alkyl group include, without limitation, 6,8-bis carbamoyl methylipoate and 6,8 methyl-succinimido lipoate.

As used herein, alkenyl refers to a $C_mH_{2m-1}$ group, wherein m is 2-10, i.e., an alkenyl group linked to the carbon backbone of formula (I) through a thio-ether linkage. Alkenyl groups can be either aliphatic (straight or branched chain) or alicyclic; alicyclic groups may have additions or substitutions on any of the carbons to form heterocyclics. At least one heteroatom such as N, O or S may be present in a given alkenyl group, i.e., in the carbon chain. Alkenyl groups may be substituted or unsubstituted on any of their carbons. Examples of alkenyl groups include, without limitation, propenyl, 2,3 dimethyl-2-butenyl, heptenyl and cyclopentenyl.

As used herein, alkynyl refers to a $C_mH_{2m-3}$, where m is 2-10, i.e., an alkynyl group linked to the carbon backbone of formula (I) through a thio-ether linkage. Alkynyl groups can be either aliphatic (straight or branched chain) or alicyclic; alicyclic groups may have additions or substitutions on any of the carbons to form heterocyclics. At least one heteroatom such as N, O or S may be present in a given alkynyl group, i.e., in the carbon chain. Alkynyl groups may be substituted or unsubstituted on any of their carbons. Examples of alkynyl groups include, without limitation, acetylenyl, propynyl and octynyl.

As used herein, aryl refers to an aromatic or aryl group linked to the carbon backbone of formula (I) through a thio-ether linkage. Aryl is preferably an unsaturated ring system having 6-10 carbon atoms. Aryl also includes organometallic aryl groups such as ferrocene. Aryl groups may be substituted or unsubstituted on any of their carbons. Examples of aryl groups include, without limitation, benzyl (—$CH_2C_6H_5$), benzyl derivatives such as methylbenzyl and aminobenzyl, (1,2,3,4,5-pentafluorophenyl)methyl, triphenylmethyl, 4-methy benzoic acid, ferrocene methyl, 2-naphthylmethyl, 4,4-biphenylmethyl, and stilbene (or 1-((1E)-2-phenylvinyl)-4-methyl benzene). A specific example of a lipoic acid derivative containing an aryl group is bis-benzyl lipoate.

As used herein, heteroaryl refers to an aromatic heterocyclic ring system (monocyclic or bicyclic) where the heteroaryl moieties are five or six membered rings containing 1 to 4 heteroatoms selected from the group consisting of S, N, and O; the heteroaryl group is linked to the carbon backbone of formula (I) through a thio-ether linkage. Heteroaryl groups may be substituted or unsubstituted on any of their atoms especially on the carbon atoms. Examples of heteroaryl groups include, without limitation, benzothiazole, quinoline, 7-chloroquinoline, furan, thiophene, indole, azaindole, oxazole, thiazole, isoxazole, isothiazole, imidazole, N-methylimidazole, pyridine, pyrimidine, pyrazine, pyrrole, N-methylpyrrole, pyrazole, N-methylpyrazole, 1,3,4-oxadiazole, 1,2,4-triazole, 1-methyl-1,2,4-triazole, 1H-tetrazole, 1-methyltetrazole, benzoxazole, benzofuran, benzisoxazole, benzimidazole, N-methylbenzimidazole, azabenzimidazole, indazole, quinazoline and pyrrolidinyl.

As used herein, alkyl sulfide refers to a $CH_3(CH_2)_n$—S— group, where n is 0-9. In other words, an alkyl group is linked to the carbon backbone of formula (I) through a disulfide linkage. The alkyl group (i.e., $CH_3(CH_2)_n$) can be substituted or unsubstituted on any of its carbons and shares the same features as set forth above with regard to the $C_nH_{2n+1}$ alkyl group.

As used herein, imidoyl refers to a $R_3C(=NH)$— group, where $R_3$ can be, without limitation, hydrogen, alkyl, alkenyl, alkynyl, cycloalkyl, aryl, alkylaryl, heteroaryl, or heterocyclyl, any of which can be substituted or unsubstituted. In other words, one of the listed $R_3$ groups is linked to the carbon backbone of formula (I) through a thio-imide linkage.

As used herein, hemiacetal refers to an $R_4CH(OH)$—S— group, where $R_4$ is a compound with strongly electron withdrawing substituents such as, without limitation, $CF_3$, $CCl_3$ or COOH.

Any of the above-described groups can be unsubstituted or substituted. Exemplary substituents include, without limitation, alkyl, alkenyl, alkynyl, aryl, heteroaryl, acyl, alkoxycarbonyl, alkoxy, alkoxyalkyl, alkoxyalkoxy, cyano, halogen, hydroxy, nitro, oxo, trifluoromethyl, trifluoromethoxy, trifluoropropyl, amino, amido, alkylamino, dialkylamino, dialkylaminoalkyl, hydroxyalkyl, alkoxyalkyl, alkylthio, —$SO_3H$, —$SO_2NH_2$, —$SO_2NHalkyl$, —$SO_2N(alkyl)_2$, —$CO_2H$, $CO_2NH_2$, $CO_2NHalkyl$, and —$CO_2N(alkyl)_2$. In addition, any number of substitutions may be made on any of the above-described groups; in other words, it is possible to have a mono-, di-, tri-, etc. substituted $R_1$ or $R_2$ group, and the substituents themselves may also be substituted. Further, any of the $R_1$ or $R_2$ groups may be appropriately generally substituted with any of a carbohydrate, a lipid, a nucleic acid, an amino acid or a polymer of any of those, or a single or branched chain synthetic polymer (having a molecular weight ranging from about 350 to about 40,000).

For any definition of $R_1$ and $R_2$ noted above, the thio-ester or thio-ether linkage by which the $R_1$ and $R_2$ are linked to the backbone can be oxidized to produce sulfoxides or sulfones; in other words, the —S— in the linkage could be —S(O)— or —$S(O)_2$. In addition, for any definition of $R_1$ and $R_2$ noted above, the thio-ester or thio-ether linkage by which the $R_1$ and $R_2$ are linked to the backbone may further comprise disulfides that can be oxidized to thiosulfinic or thiosulfonic acids; in other words, instead of —S— in a linkage, the linkage could be —S(O)—S— or —$S(O)_2$—S—.

In another preferred embodiment of this invention, the lipoic acid derivative has the formula (II):

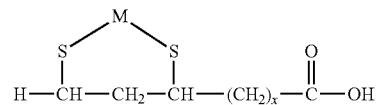

M is a metal chelate, —$[C(R_1)(R_2)]_z$— or other metal complex. $R_1$ and $R_2$ are independently selected from the group consisting of acyl defined as $R_3C(O)$—, alkyl defined as $C_nH_{2n+1}$, alkenyl defined as $C_mH_{2m-1}$, alkynyl defined as $C_mH_{2m-3}$, aryl, heteroaryl, alkyl sulfide defined as $CH_3(CH_2)_n$—S—, imidoyl defined as $R_3C(=NH)$—, hemiacetal defined as $R_4CH(OH)$—S— and hydrogen, wherein $R_1$ and $R_2$ as defined above can be unsubstituted or substituted. $R_3$ is hydrogen, alkyl, alkenyl, alkynyl, cycloalkyl, aryl, alkylaryl, heteroaryl, or heterocyclyl, any of which can be substituted or unsubstituted; $R_4$ is $CCl_3$ or COOH. In addition, x is 0-16, z is preferably 0-5, more preferably 0-3, n is 0-10 and m is 2-10. Suitable —$[C(R_1)(R_2)]_z$— groups include, without limitation, —$CH_2$—, —$CH(CH_3)$—, —$C(CH_3)_2$—, —$CH(C_6H_5)$— and —CH(pyridine).

Also in this embodiment, a metal or metal salt can be added to one or both sulfhydryls through a bond in which a metal or metal salt forms a covalent or coordination or chelated complex with the thiol group(s) of the lipoic acid molecule. Such metals include, platinum, nickel, silver, rhodium, cadmium, gold, palladium or cobalt. Metal salts include, for example, platinum bromide, platinum chloride, platinum iodide, nickel borate, nickel boride, nickel bromide, nickel chloride, nickel iodide, nickel fluoride, silver bromate, silver bromide, silver chloride, silver fluoride, silver iodide, rhodium chloride, cadmium bromide, cadmium chloride, cadmium fluoride, cadmium iodide, gold bromide, gold chloride, gold iodide, cobalt bromide, cobalt bromide, cobalt chloride, cobalt fluoride, cobalt iodide, palladium chloride, palladium iodide, and palladium bromide. Such salts include various metal oxidation states such as, for example, platinum (II) chloride and platinum (IV) chloride. In general, the structure of the lipoic acid-metal complex described herein is likely to be (metal)$_m$(lipoic acid)$_n$ where m and n are both one or where m is one and n is two.

Regardless of whether the lipoic acid derivative is of formula (I) or formula (II), pharmaceutical formulations of the present invention may include lipoic acid derivatives in which one or both of the thiols have been replaced with a selenium molecule, a sulfur analog, or in which one or both of the thiols have been oxidized to sulfate or related groups.

In particularly preferred embodiments of the present invention, the lipoic acid derivative is one selected from the following:

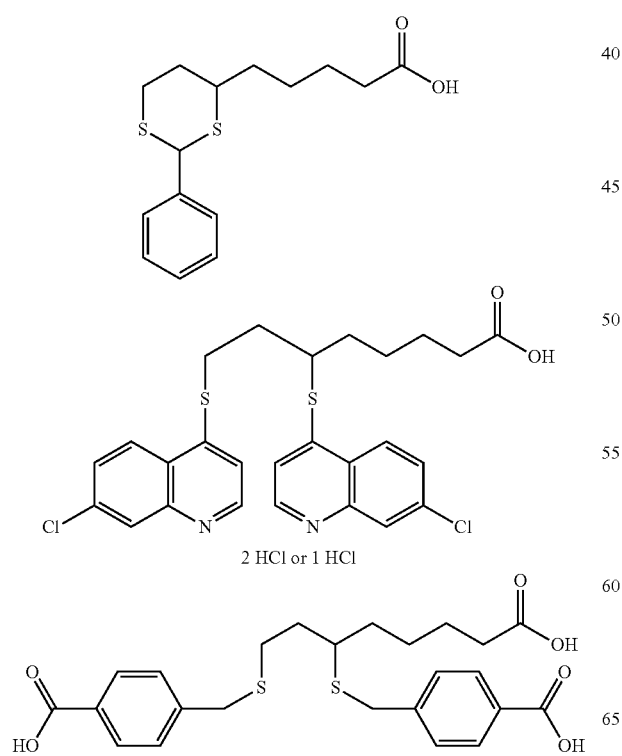

-continued

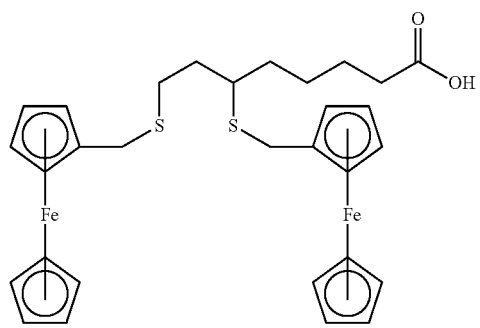

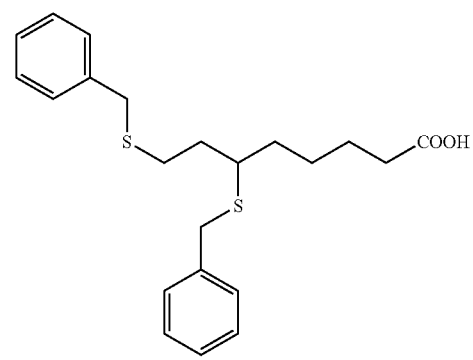

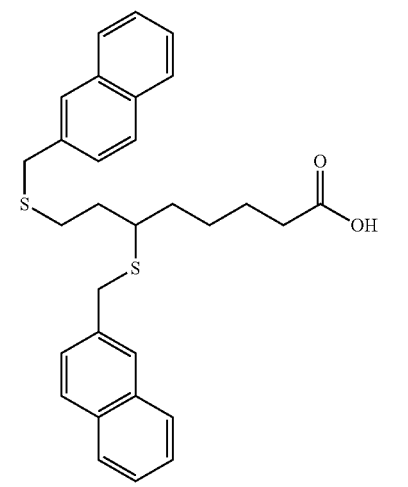

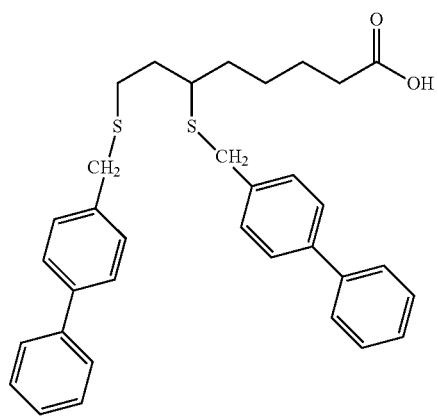

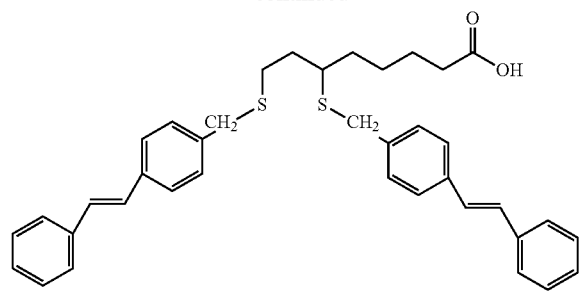
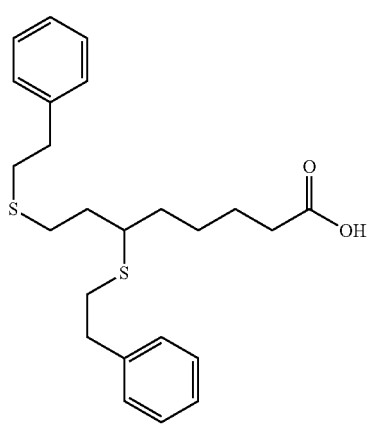
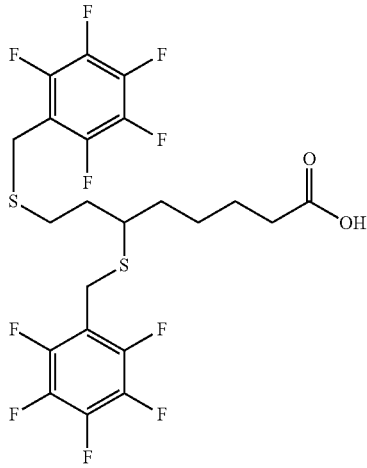
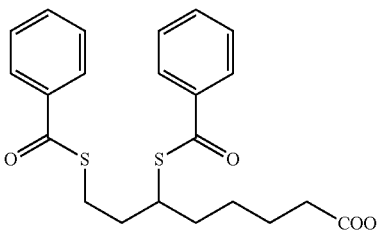
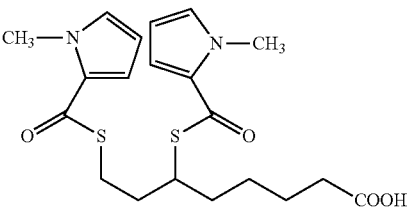
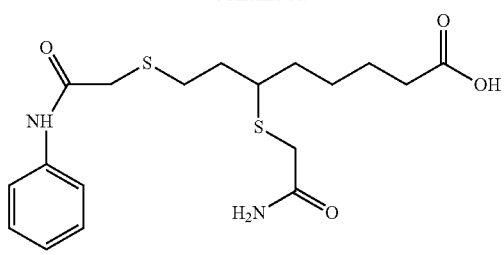
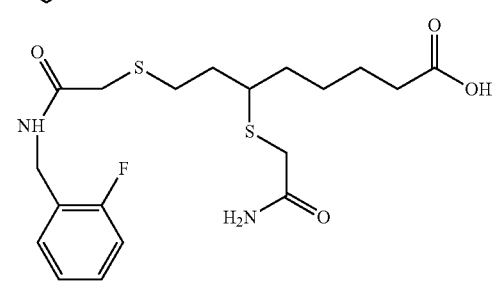
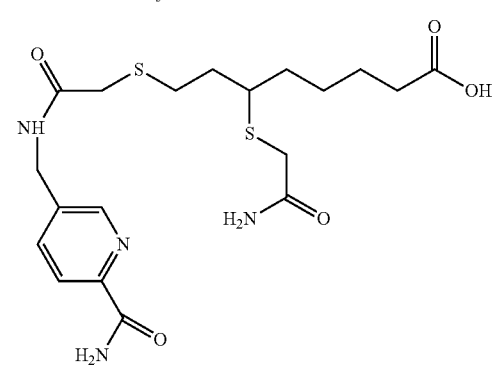
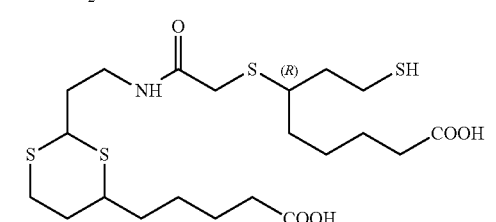
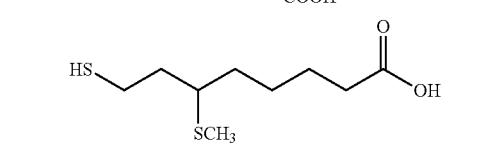
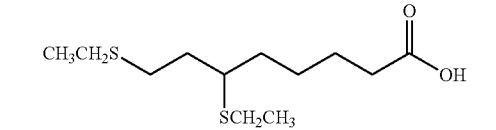

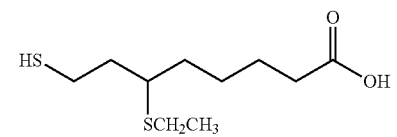
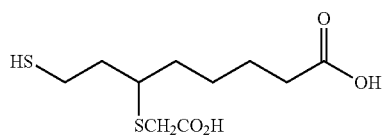
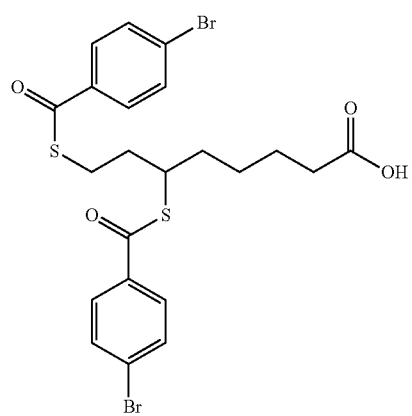
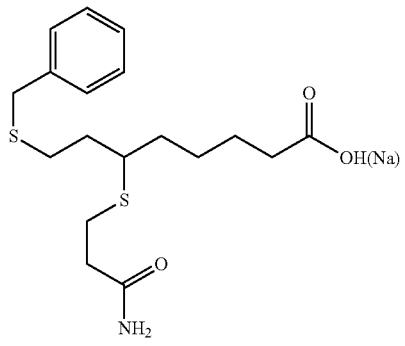
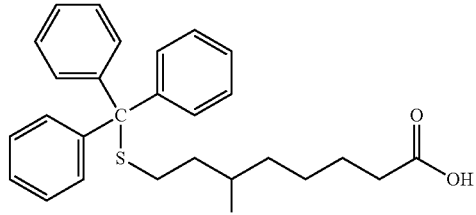
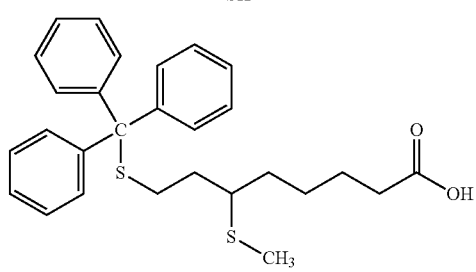
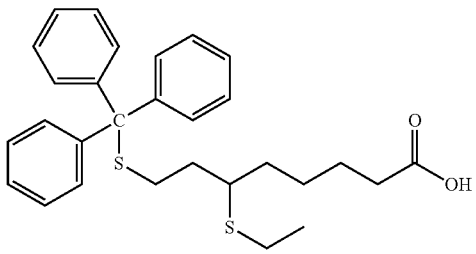
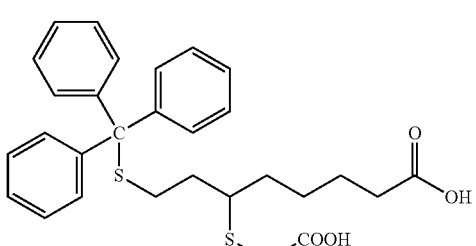
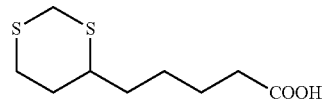
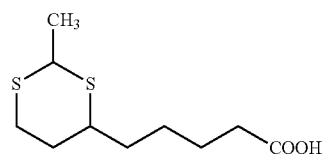
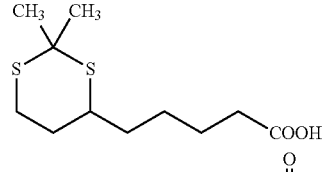
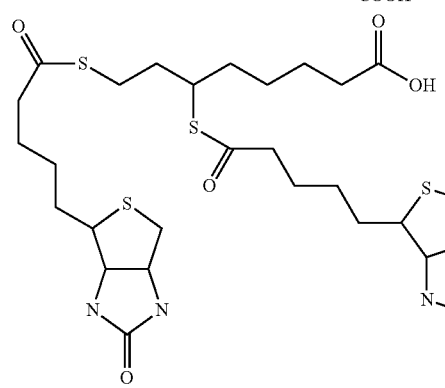
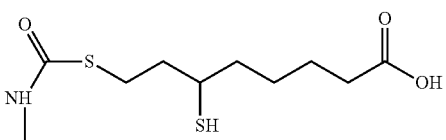
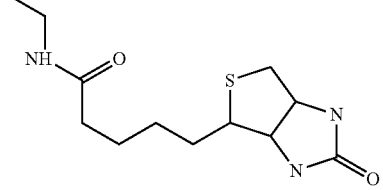

-continued
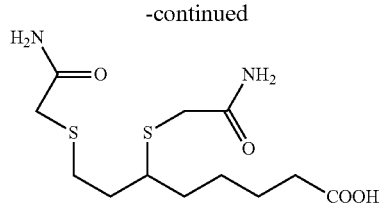
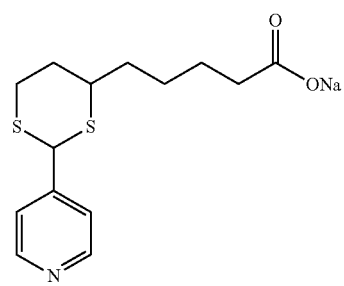
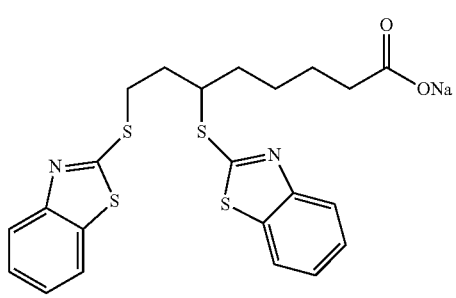
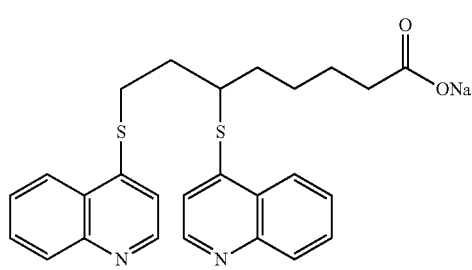
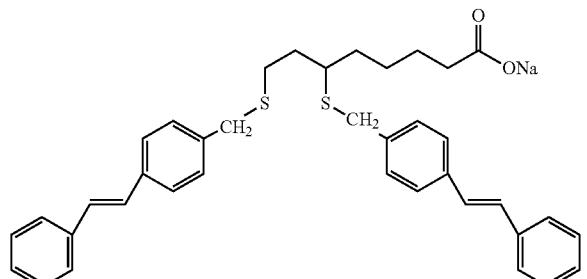
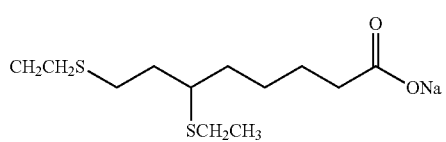
-continued
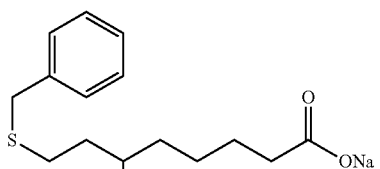
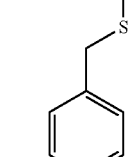
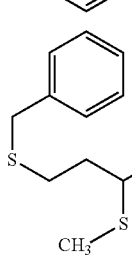
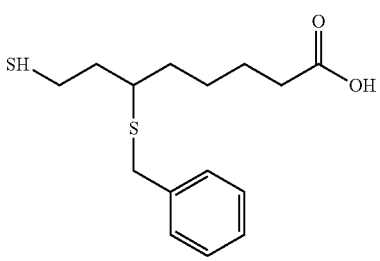
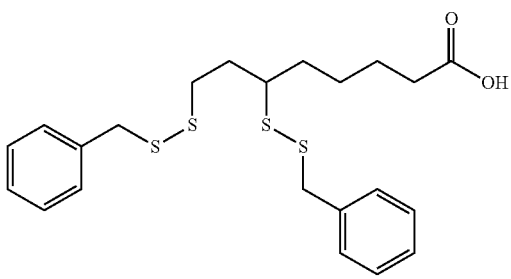
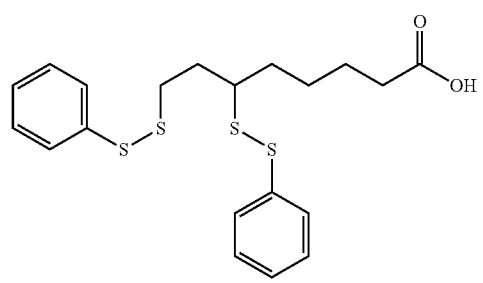
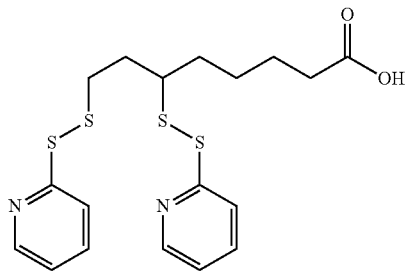

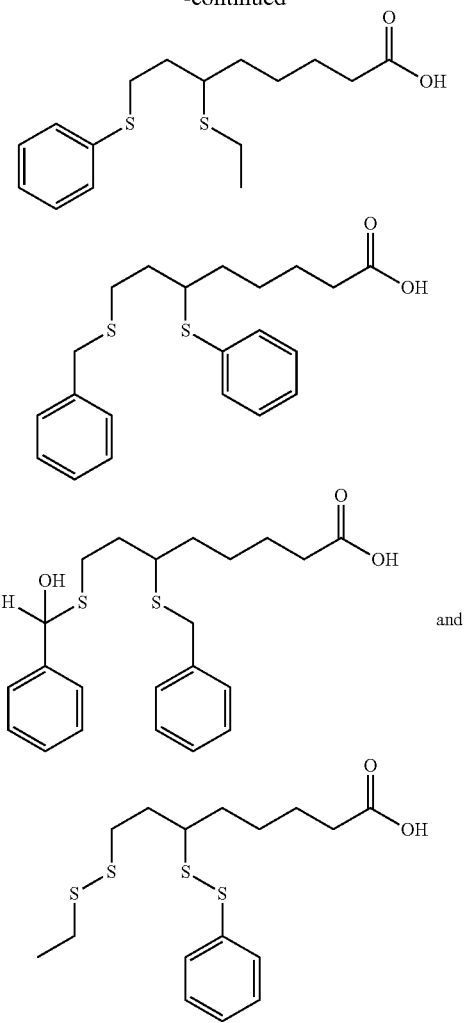

or a salt thereof (if not already in salt form).

When the at least one lipoic acid derivative is a salt, it may be necessary to perform ion exchange in order to achieve ion pairing in accordance with the invention. However, if a weak salt is used, an ion pairing agent such as triethanolamine could displace the anion without the need for ion exchange.

Typically the at least one lipoic acid derivative is present in a pharmaceutical formulation of the present invention in a therapeutically effective amount. The pharmaceutical formulation of the present invention may contain a unit dose or multiple doses of the lipoic acid derivative. A "therapeutically effective amount" is intended to mean the amount of a lipoic acid derivative that, when administered to a subject in need thereof, is sufficient to effect treatment for (or prevent) disease conditions characterized by disease cells that are sensitive to lipoic acid derivatives. The amount of a given lipoic acid derivative that will be therapeutically effective will vary depending upon factors such as the disease condition and the severity thereof, the identity of the subject in need thereof, etc., which amount may be routinely determined by those of ordinary skill in the art. Importantly, the quantity of lipoic acid derivative in a unit dose should be sufficient to inhibit or kill tumor cells while leaving normal cells substantially unharmed. The at least one lipoic acid derivative is preferably present in a pharmaceutical formulation of the present invention in an amount to provide from about 0.001 mg/m$^2$ to about 10 g/m$^2$, more preferably about 0.01 mg/m$^2$ to about 5 g/m$^2$, still more preferably from about 0.25 mg/m$^2$ to about 3 g/m$^2$, and most preferably from about 20 mg/m$^2$ to about 500 mg/m$^2$ of the at least one lipoic acid derivative per dose.

Importantly, the pharmaceutical formulations of the present invention includes at least one ion pairing agent. As used herein, "ion pairing agent" refers to any agent which is capable of forming a "salt bridge" or an "ion pair" with a given lipoic acid derivative. As used herein, "salt bridge" or "ion pair" refers to not only a salt (weak or strong) formed between an ion pairing agent and a given lipoic acid derivative, but also to other ionic associations (weak or strong) that do not rise to the level of actual salt formation between an ion pairing agent and a given lipoic acid derivative. Without being bound by theory, it is believed that an ion pairing agent such as triethanolamine forms a salt bridge, i.e., forms a salt in situ, with a lipoic acid derivative such as bis-benzyl lipoate, which then enables the lipoic acid deriviative to achieve its cell kill effect in vivo.

Ion pairing agents particularly suitable for use in the present invention include, without limitation, tertiary amines such as triethanolamine and polyethyleneimine, other amines such as diethanolamine, monoethanolamine, mefenamic acid and tromethamine, and combinations thereof. A preferred ion pairing agent is triethanolamine. Additional ion pairing agents suitable for use in this invention include polymer-conjugated ion pairing agents which employ, without limitation, polyethylene glycol, polyglutamic acid and sugar-based polymers such as dextrans in combination with any of the above-noted ion pairing agents or any other known ion pairing agent. Still further ion pairing agents can be selected with guidance from Handbook of Pharmaceutical Salts: Properties, Selection and Use, IUPAC, Wiley-VCH, P. H. Stahl, ed., the entire disclosure of which is incorporated by reference herein. Ion pairing agents of particular note therein include, without limitation, those listed in Table 5, p. 342, i.e., ammonia, L-arginine, benethamine benzathine, betaine, calcium hydroxide, choline, deanol, diethanolamine(2,2'-iminobis (ethanol)), diethylamine, 2-(diethylamino)-ethanol, ethanolamine, ethylenediamine, N-methyl-glucamine, hydrabamine, 1H-imidazole, lysine, magnesium hydroxide, 4-(2-hydroxyethyl)-morpholine, pperazine, potassium hydroxide, 1-(2-hydroxyethyl)-pyrrolidine, sodium hydroxide, triethanolamine (2,2',2"-nitrilotris(ethanol)), tromethamine, and zinc hydroxide.

The ion pairing agent may be hydrophilic or hydrophobic (such as acylated triethanolamine). Typically the ion pairing agent is present in an amount sufficient to achieve substantial solubility of the at least one lipoic acid derivative in a solvent suitable for intravenous administration, which is most preferably an aqueous medium. Preferably the ion pairing agent and lipoic acid derivative are present in a molar ratio ranging from about 1000:1 to about 1:1000, more preferably from about 500:1 to about 1:500, still more preferably from about 50:1 to about 1:50, still further more preferably from about 20:1 to about 1:20, and most preferably of about 1:1.

The pharmaceutical formulations of the present invention optionally include (c) a pharmaceutically acceptable diluent. In particular, when a pharmaceutical formulation suitable for, e.g., intravenous administration is desired, a suitable diluent would be employed. Any conventional aqueous or polar aprotic solvent is suitable for use in the present invention. Suitable pharmaceutically acceptable diluents include, without limitation, saline, a sugar solution, alcohols such as ethyl alcohol, methanol and isopropyl alcohol, polar aprotic solvents such as dimethylformamide (DMF), dimethylsulfoxide (DMSO) and dimethylacetamide (DMA), and combinations thereof. A preferred pharmaceutically acceptable diluent is a dextrose solution, more preferably a dextrose solution containing from about 2.5% to about 10%, more preferably about 5%, dextrose by weight. The pharmaceutically acceptable diluent is typically employed in a non-homolysis generating amount; one of ordinary skill in the art can readily determine an amount of diluent suitable for use in a pharmaceutical formulation according to the present invention.

In a highly preferred embodiment of the present invention, the pharmaceutical formulation comprises bis-benzyl lipoate, triethanolamine and a dextrose solution containing about 5% dextrose by weight.

The pharmaceutical formulations of the present invention may optionally include at least one other pharmaceutically acceptable additive. Suitable additives include, without limitation, solvents, diluents, surfactants, solubilizers, preservatives, buffers, and combinations thereof, as well as any other additives particularly suited for use in parenteral administration forms. It is well within the skill of one of ordinary skill in the art to determine suitable amounts of these other pharmaceutically acceptable additives. Solvents particularly suitable for use herein include benzyl alcohol, dimethylamine, isopropyl alcohol and combinations thereof; one of ordinary skill in the art would readily recognize that it may be desirable to first dissolve the at least one lipoic acid derivative in a suitable solvent and then to dilute the solution into an ion pairing agent and finally to dilute with a diluent.

The pharmaceutical formulations of the present invention can be prepared according to conventional formulation techniques. For example, a stock solution of the at least one lipoic acid derivative and the ion pairing agent can be prepared according to conventional techniques and then diluted as desired by a pharmaceutically acceptable diluent.

The pharmaceutical formulations of the present invention are liquid preparations such as sterile parenteral solutions. The pharmaceutical formulations of the present invention may be contained in any suitable vessel such as a vial or ampoule and are suitable for administration via one of several routes including, without limitation, intravenous, intramuscular, subcutaneous, intradermally, intraperitoneal, intrathoracic, intrapleural, intrauterine or intratumor.

A second embodiment of the invention is directed to a method of treating a disease characterized by disease cells that are sensitive to lipoic acid derivatives comprising administering to a patient in need thereof a pharmaceutical formulation according to the first embodiment of the invention. A third embodiment of the invention is directed to a method of preventing a disease characterized by disease cells that are sensitive to lipoic acid derivatives comprising administering to a patient in need thereof a pharmaceutical formulation according to the first embodiment of the invention.

According to the second and third embodiments, pharmaceutical formulations of lipoic acid derivatives may be used to prevent or inhibit diseases involving altered or distinct cellular PDC activity, i.e., diseases characterized by disease cells that are sensitive to lipoic acid derivatives. Cells with appropriately altered or deranged energy metabolism, i.e., altered PDC activity, are particularly targeted and killed, while surrounding healthy tissues remain unharmed by the lipoic acid derivative. The skilled artisan can readily identify diseases having altered PDC activity. Alternatively, the skilled artisan can readily screen the disease of interest for sensitivity to lipoic acid derivatives.

In preferred embodiments of the methods of the present invention, the disease treated or prevented includes cancer, such as carcinoma, sarcoma, myeloma, lymphoma, leukemia and mixed types thereof. The pharmaceutical formulations of the present invention are effective against both primary and metastatic cancers and effective against cancers of the, without limitation, lung, liver, uterus, cervix, bladder, kidney, colon, breast, prostate, ovary, and pancreas. In other embodiments, the pharmaceutical formulations of the present invention can be used in the treatment of diseases associated with altered energy metabolism such as Alzheimer's disease, hyperproliferative diseases such as psoriasis and other diseases such as diabetic neuropathy.

For therapeutic applications, a pharmaceutical formulation according to the first embodiment of the invention is administered directly to a patient, typically in a unit dose form. In the methods of this invention, the pharmaceutical formulation comprising the lipoic acid derivative may be administered via one of several routes including, without limitation, intravenous, intramuscular, subcutaneous, intradermally, intraperitoneal, intrathoracic, intrapleural, intrauterine or intratumor. Those skilled in the art will recognize that the mode of administering the lipoic acid derivative depends on the type of cancer or symptom to be treated. For example, a preferred mode of administering the lipoic acid for treatment of leukemia would involve intravenous administration. Likewise, those skilled in the art will also recognize that particular pharmaceutically acceptable additives will vary from pharmaceutical formulations suitable for one administration mode to pharmaceutical formulations suitable for another administration mode—the constant in all pharmaceutical formulations regardless of intended mode of administration, however, is the presence of an ion pair formed between the at least one lipoic acid derivative and the ion pairing agent.

By adapting the treatments described herein, the pharmaceutical formulations of the present invention may also be used in methods for treating diseases other than cancer, where the disease-causing cells exhibit altered metabolic patterns. For example, eukaryotic pathogens of humans and other animals are generally much more difficult to treat than bacterial pathogens because eukaryotic cells are so much more similar to animal cells than are bacterial cells. Such eukaryotic pathogens include protozoans such as those causing malaria as well as fungal and algal pathogens. Because of the remarkable lack of toxicity of the lipoic acid derivatives used in the invention to normal human and animal cells and because many eukaryotic pathogens are likely to pass through life cycle stages in which their PDCs become sensitive to lipoic acid derivatives, the pharmaceutical formulations of the present invention can be used to kill bacterial PDCs.

Yet another embodiment of the present invention is directed to an ion pair, be it a true salt or some other lesser ionic association, consisting of (a) at least one lipoic acid derivative and (b) an ion pairing agent. In a highly preferred embodiment, the ion pair consists of bis-benzyl lipoate and triethanolamine. The present invention includes all ion pairs, whether in situ as formed or isolated by some conventional method. All of the details regarding amounts of (a) and (b) and possible materials suitable for use are the same as those set forth above with regard to the first embodiment.

Specific embodiments of the invention will now be demonstrated by reference to the following examples. It should be understood that these examples are disclosed solely by way of illustrating the invention and should not be taken in any way to limit the scope of the present invention.

EXAMPLE 1

Bis-benzyl lipoate was provided in a concentrated form at a concentration of 50 mg/mL dissolved in 1M triethanolamine (TEA). The stability of the drug product was assessed by visual observation and by high-performance liquid chromatography (HPLC) assessment, performed at the beginning and the end of the study. The physical appearance did not change and the purity was found to be >99% pure, both at the beginning and the end of the study. The concentrated bis-benzyl lipoate solution was diluted to an appropriate concentration with 5% dextrose (D5W) to formulate 0.1, 1 and 10 mg/kg doses of bis-benzyl lipoate.

COMPARATIVE EXAMPLE 1

Bis-benzyl lipoate was dissolved to a concentration of 40 mg/mL in a conventional mixture of Tween 80 and ethanol (1:1 by volume ratio). The concentrated bis-benzyl lipoate solution was diluted to an appropriate concentration with saline.

TESTING

A study to assess the dose and dosing schedule effects on the anti-tumor activity of bis-benzyl lipoate was undertaken. More specifically, the pharmaceutical formulations of bis-benzyl lipoate of Comparative Example 1, i.e., bis-benzyl lipoate dissolved in 1:1 Tween 80:ethanol and diluted with saline, were tested in mice with Human H-460 Non Small Cell Lung Carcinoma (NSCLC) xenograft. The pharmaceutical formulations were administered intraperitoneally (IP), given 1× or 3× weekly. Administration of bis-benzyl lipoate began when the average tumor size of the mice was ~300 mm³. There were originally eight treatment groups, with seven mice in each group, investigating three doses (0.1, 1 and 10 mg/kg) and two dosing schedules, as shown in Table 1 below.

TABLE 1

Original Treatment Groups.

| Treatment Group | Dose of bis-benzyl lipoate (mg/kg) | Dose Schedule | # of mice |
|---|---|---|---|
| 1 | 0 (vehicle*) | 1× weekly | 7 |
| 2 | 0 (vehicle*) | 3× weekly | 7 |
| 3 | 0.1 | 1× weekly | 7 |
| 4 | 0.1 | 3× weekly | 7 |
| 5 | 1 | 1× weekly | 7 |
| 6 | 1 | 3× weekly | 7 |
| 7 | 10 | 1× weekly | 7 |
| 8 | 10 | 3× weekly | 7 |

*vehicle refers to a Tween 80/ethanol/saline mixture

The results (as shown in FIGS. 1A and 1B) showed that bis-benzyl lipoate did not induce any anti-tumor effects, when compared to vehicle treatment.

Next, the protocol was revised by subdividing each treatment group into two subgroups, as shown in Table 2 below. Specifically, both subgroups of each treatment group were treated with the same dose of bis-benzyl lipoate as in the original protocol; however, one of the two subgroups was treated with a pharmaceutical formulation of bis-benzyl lipoate according to Comparative Example 1, i.e., bis-benzyl lipoate dissolved in 1:1 Tween 80:ethanol and diluted with saline, and the other subgroup was treated with a pharmaceutical formulation of bis-benzyl lipoate according to Example 1, i.e., dissolved in TEA and diluted with D5W.

TABLE 2

Revised Treatment Groups.

| Group | | Bis-benzyl lipoate (mg/kg) | Dose Schedule | Vehicle | #mice |
|---|---|---|---|---|---|
| 1 & 2 | A | 0.1 | 1× weekly | TEA | 4 |
| | B | 1 | 1× weekly | TEA | 3 |
| | A | 10 | 1× weekly | TEA | 4 |
| | B | 10 | 1× weekly | Tween 80:Ethanol | 3 |
| 3 | A | 0.1 | 1× weekly | Tween 80:Ethanol | 4 |
| | B | 0.1 | 1× weekly | TEA | 3 |
| 4 | A | 0.1 | 3× weekly | Tween 80:Ethanol | 4 |
| | B | 0.1 | 3× weekly | TEA | 3 |
| 5 | A | 1 | 1× weekly | Tween 80:Ethanol | 3 |
| | B | 1 | 1× weekly | TEA | 4 |
| 6 | A | 1 | 3× weekly | Tween 80:Ethanol | 3 |
| | B | 1 | 3× weekly | TEA | 4 |
| 7 | A | 10 | 1× weekly | Tween 80:Ethanol | 4 |
| | B | 10 | 1× weekly | TEA | 3 |
| 8 | A | 10 | 3× weekly | Tween 80:Ethanol | 4 |
| | B | 10 | 3× weekly | TEA | 3 |

The results showed that H-460 tumors in mice treated with 0.1-10 mg/kg of bis-benzyl lipoate in pharmaceutical formulations made according to Example 1 may be similar among each other, but may be smaller than that in mice treated with 10 mg/kg of bis-benzyl lipoate in a pharmaceutical formulation made according to Comparative Example 1.

Next, again the protocol was revised to change the pharmaceutical formulation tested for anti-tumor efficacy to exclusively pharmaceutical formulations made according to Example 1, i.e., dissolved in TEA and diluted with D5W. There were ten treatment groups, with 8 mice in each group, investigating three doses (0.1, 1 and 10 mg/kg) and three dosing schedules, as shown in Table 3 below.

TABLE 3

Second Revised Treatment Groups.

| Treatment Group | Dose of bis-benzyl lipoate (mg/kg) | Dose Schedule | # of mice |
|---|---|---|---|
| 1 | 0 (vehicle*) | 5× weekly | 8 |
| 2 | 0.1 | 1× weekly | 8 |
| 3 | 0.1 | 3× weekly | 8 |
| 4 | 0.1 | 5× weekly | 8 |
| 5 | 1 | 1× weekly | 8 |
| 6 | 1 | 3× weekly | 8 |
| 7 | 1 | 5× weekly | 8 |
| 8 | 10 | 1× weekly | 8 |
| 9 | 10 | 3× weekly | 8 |
| 10 | 10 | 5× weekly | 8 |

*vehicle refers to D5W only

Figures 2A, 2B, 2C:
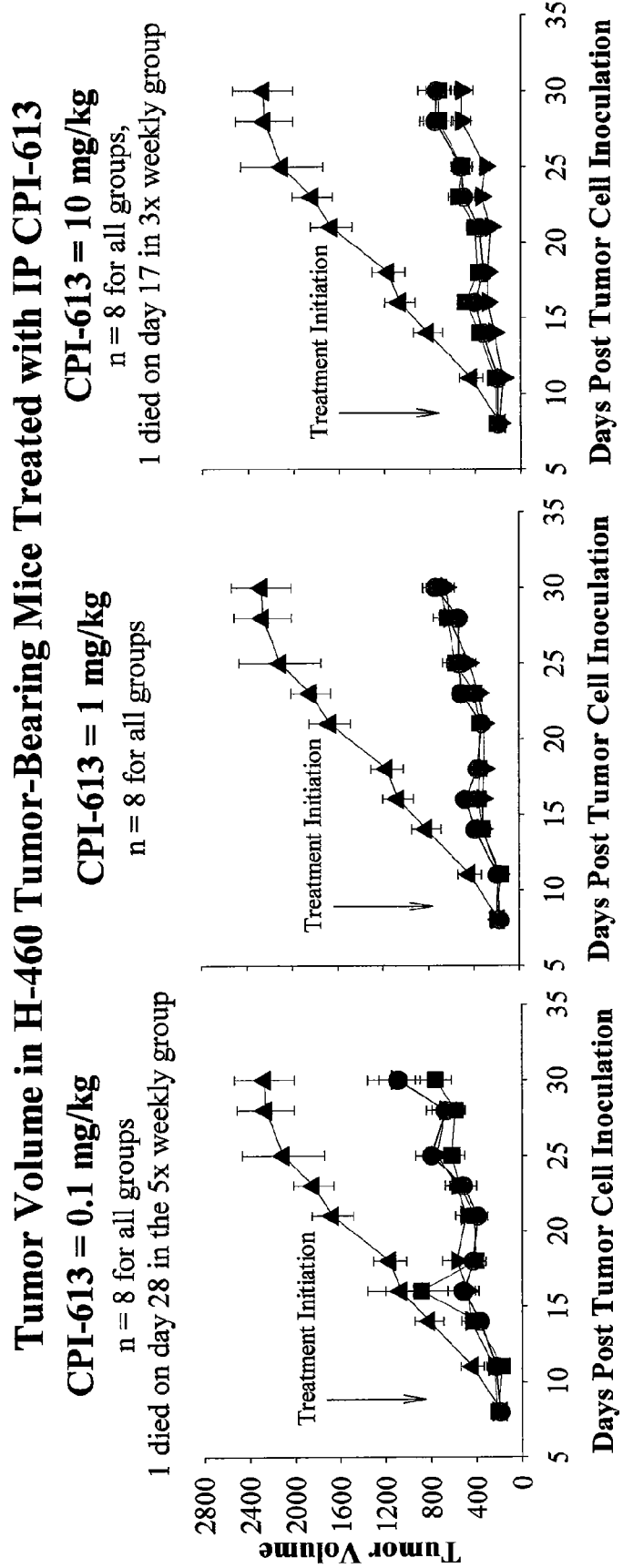
FIGS. 2A, 2B and 2C show the tumor volume in H-460 tumor-bearing mice treated with bis-benzyl lipoate in a triethanolamine/dextrose pharmaceutical formulation at 3 different dosage levels.

The results (as shown in FIGS. 2A-2C) showed that bis-benzyl lipoate in pharmaceutical formulations prepared according to Example 1 (TEA/D5W) at 0.1, 1 and 10 mg/kg, given 1×, 3× or 5× weekly induced a similar and significant degree of tumor growth inhibition as compared with the results obtained when pharmaceutical formulations prepared according to Comparative Example 1 (Tween 80/ethanol/saline) were similarly tested.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entirety.

What is claimed is:

1. A method of treating leukemia, comprising administering to a patient in need thereof to treat the leukemia a therapeutically effective amount of a pharmaceutical formulation comprising:

(a) a compound of Formula I:

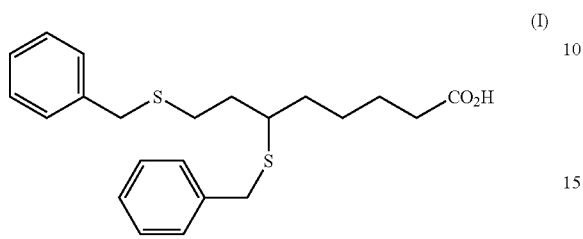

(b) triethanolamine; and
(c) a pharmaceutically acceptable diluent;
wherein the compound of Formula I and triethanolamine form an ion pair.

2. The method of claim 1, wherein the diluent is selected from the group consisting of saline, a sugar solution, an alcohol, dimethylformamide, dimethylsulfoxide, dimethylacetamide, and combinations thereof.

3. The method of claim 1, wherein the diluent is a dextrose solution.

4. The method of claim 3, wherein the dextrose solution contains an amount of dextrose ranging from about 2.5% to about 10% by weight.

* * * * *